(12) United States Patent
Sweeney

(10) Patent No.: US 6,950,702 B2
(45) Date of Patent: Sep. 27, 2005

(54) USE OF CURVATURE BASED FEATURES FOR BEAT DETECTION

(75) Inventor: Robert J. Sweeney, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 413 days.

(21) Appl. No.: 10/195,838

(22) Filed: Jul. 15, 2002

(65) Prior Publication Data

US 2004/0010200 A1 Jan. 15, 2004

(51) Int. Cl.$^7$ .................. A61N 1/362; A61B 5/0452

(52) U.S. Cl. .................................. 607/26; 600/510

(58) Field of Search .................. 607/4–28; 600/508–521

(56) References Cited

U.S. PATENT DOCUMENTS

| | | | |
|---|---|---|---|
| 4,023,564 A | 5/1977 | Valiquette et al. | |
| 4,336,810 A | 6/1982 | Anderson et al. | |
| 4,531,527 A | 7/1985 | Reinhold, Jr. et al. | |
| 4,583,553 A | 4/1986 | Shah et al. | |
| 4,721,114 A | 1/1988 | DuFault et al. | |
| 4,802,491 A | 2/1989 | Cohen et al. | |
| 4,809,697 A | 3/1989 | Causey, III et al. | |
| 4,825,869 A | 5/1989 | Sasmor et al. | |
| 4,838,278 A | 6/1989 | Wang et al. | |
| 4,924,875 A | 5/1990 | Chamoun | |
| 4,947,857 A | 8/1990 | Albert et al. | |
| 4,989,610 A | 2/1991 | Patton et al. | |
| 5,000,189 A | 3/1991 | Throne et al. | |
| 5,014,284 A | 5/1991 | Langer et al. | |

(Continued)

FOREIGN PATENT DOCUMENTS

| | | | |
|---|---|---|---|
| DE | 4405827 | 6/1995 | |
| EP | 0469817 A2 | 2/1992 | |
| EP | 0506230 A1 | 9/1992 | |
| EP | 0554208 | 8/1993 | ......... A61B/5/0452 |
| EP | 0711531 A1 | 5/1996 | |
| EP | 0776630 A1 | 11/1996 | |
| EP | 0776631 A1 | 11/1996 | |
| EP | 0848965 A2 | 6/1998 | |
| WO | WO-97/39681 A1 | 10/1997 | |
| WO | WO-98/53879 A1 | 12/1998 | |
| WO | WO-99/65570 | 12/1999 | ............ A61N/1/39 |
| WO | WO-00/10455 | 3/2000 | ............ A61B/5/04 |
| WO | WO-00/47278 | 8/2000 | ............ A61N/1/37 |
| WO | WO-02/40094 A2 | 5/2002 | |

OTHER PUBLICATIONS

"PCT Partial Search Report for PCT Application No. PCT/US2004/020723", 2 Pages.

Duru, Firat, et al., "The Potential for Inappropriate Ventricular Tachycardia Confirmation Using the Intracardiac Electrogram (EGM) Width Criterion", *PACE*, vol. 22, 1999, (Jul. 1999), 1039–1046.

Grady, Thomas A., et al., "Prognostice Significance of Exercise–Induced Left Bundle–Branch Block", *JAMA*, vol. 279, No. 2, Jan. 14, 1998, 153–156.

(Continued)

*Primary Examiner*—Scott M. Getzow
(74) *Attorney, Agent, or Firm*—Schwegman, Lundberg, Woessner & Kluth, P.A.

(57) ABSTRACT

A cardiac rhythm management system includes a sensing circuit to sense a cardiac signal and a sensing processor to detect cardiac depolarizations (beats) by utilizing certain morphological context of the sensed cardiac signal. The sensing processor samples the sensed cardiac signal, computes curvatures from the sampled cardiac signal to generate a cardiac curvature signal corresponding to the cardiac signal, derives cardiac signal features reflecting morphologically significant points along the cardiac signal from the cardiac curvature signal, and detects cardiac depolarizations based on an analysis of the cardiac signals features.

39 Claims, 4 Drawing Sheets

U.S. PATENT DOCUMENTS

| | | |
|---|---|---|
| 5,014,698 A | 5/1991 | Cohen |
| 5,020,540 A | 6/1991 | Chamoun |
| 5,107,850 A | 4/1992 | Olive |
| 5,109,842 A | 5/1992 | Adinolfi |
| 5,139,028 A | 8/1992 | Steinhaus et al. |
| 5,156,148 A | 10/1992 | Cohen |
| 5,184,615 A | 2/1993 | Nappholz et al. |
| 5,193,550 A | 3/1993 | Duffin |
| 5,215,098 A | 6/1993 | Steinhaus et al. |
| 5,217,021 A | 6/1993 | Steinhaus et al. |
| 5,240,009 A | 8/1993 | Williams |
| 5,247,021 A | 9/1993 | Fujisawa et al. |
| 5,255,186 A | 10/1993 | Steinhaus et al. |
| 5,269,301 A | 12/1993 | Cohen |
| 5,271,411 A | 12/1993 | Ripley et al. |
| 5,273,049 A | 12/1993 | Steinhaus et al. |
| 5,275,621 A | 1/1994 | Mehra |
| 5,280,792 A | 1/1994 | Leong et al. |
| 5,292,341 A | 3/1994 | Snell |
| 5,292,348 A | 3/1994 | Saumarez et al. |
| 5,311,874 A | 5/1994 | Baumann et al. |
| 5,312,445 A | 5/1994 | Nappholz et al. |
| 5,313,953 A | 5/1994 | Yomtov et al. |
| 5,330,504 A | 7/1994 | Somerville et al. |
| 5,331,966 A | 7/1994 | Bennett et al. |
| 5,350,406 A | 9/1994 | Nitzsche et al. |
| 5,360,436 A | 11/1994 | Alt et al. |
| 5,365,934 A | 11/1994 | Leon et al. |
| 5,366,487 A | 11/1994 | Adams et al. |
| 5,388,578 A | 2/1995 | Yomtov et al. |
| 5,400,795 A | 3/1995 | Murphy et al. |
| 5,411,031 A | 5/1995 | Yomtov |
| 5,421,830 A | 6/1995 | Epstein et al. |
| 5,447,519 A | 9/1995 | Peterson |
| 5,447,524 A | 9/1995 | Alt |
| 5,456,261 A | 10/1995 | Luczyk |
| 5,458,623 A | 10/1995 | Lu et al. |
| 5,464,433 A | 11/1995 | White et al. |
| 5,478,807 A | 12/1995 | Cronin et al. |
| 5,503,159 A | 4/1996 | Burton |
| 5,509,927 A | 4/1996 | Epstein et al. |
| 5,511,554 A * | 4/1996 | Helfenbein et al. .......... 600/519 |
| 5,513,644 A | 5/1996 | McClure et al. ............ 128/708 |
| 5,520,191 A | 5/1996 | Karlsson et al. |
| 5,542,430 A | 8/1996 | Farrugia et al. |
| 5,549,654 A | 8/1996 | Powell |
| 5,560,369 A | 10/1996 | McClure et al. ............ 128/704 |
| 5,609,158 A | 3/1997 | Chan |
| 5,622,178 A | 4/1997 | Gilham |
| 5,628,326 A | 5/1997 | Arand et al. |
| 5,634,468 A | 6/1997 | Platt et al. |
| 5,645,070 A | 7/1997 | Turcott |
| 5,682,900 A | 11/1997 | Arand et al. |
| 5,683,425 A | 11/1997 | Hauptmann |
| 5,685,315 A | 11/1997 | McClure et al. ............ 128/708 |
| 5,687,737 A | 11/1997 | Branham et al. |
| 5,704,365 A | 1/1998 | Albrecht et al. |
| 5,712,801 A | 1/1998 | Turcott |
| 5,713,366 A | 2/1998 | Armstrong et al. |
| 5,713,367 A | 2/1998 | Arnold et al. |
| 5,718,242 A | 2/1998 | McClure et al. ............ 600/515 |
| 5,724,985 A | 3/1998 | Snell et al. |
| 5,730,142 A | 3/1998 | Sun et al. |
| 5,738,105 A | 4/1998 | Kroll |
| 5,755,739 A | 5/1998 | Sun et al. ...................... 607/14 |
| 5,759,158 A | 6/1998 | Swanson |
| 5,772,604 A | 6/1998 | Langberg et al. |
| 5,778,881 A | 7/1998 | Sun et al. |
| 5,779,645 A | 7/1998 | Olson et al. |
| 5,782,888 A | 7/1998 | Sun et al. |
| 5,792,065 A | 8/1998 | Xue et al. |
| 5,792,066 A | 8/1998 | Kwong ...................... 600/517 |
| 5,795,303 A | 8/1998 | Swanson et al. |
| 5,797,399 A | 8/1998 | Morris et al. |
| 5,797,849 A | 8/1998 | Vesely et al. |
| 5,817,133 A | 10/1998 | Houben |
| 5,819,007 A | 10/1998 | Elghazzawi |
| 5,819,741 A | 10/1998 | Karlsson et al. |
| 5,827,195 A | 10/1998 | Lander ...................... 600/509 |
| 5,848,972 A | 12/1998 | Triedman et al. |
| 5,857,977 A | 1/1999 | Caswell et al. |
| 5,858,977 A | 1/1999 | Aukerman et al. |
| 5,868,680 A | 2/1999 | Steiner et al. |
| 5,935,082 A | 8/1999 | Albrecht et al. |
| 5,954,661 A | 9/1999 | Greenspon et al. |
| 5,957,857 A | 9/1999 | Hartley ...................... 600/524 |
| 6,024,705 A | 2/2000 | Schlager et al. |
| 6,108,577 A | 8/2000 | Benser ...................... 600/517 |
| 6,212,428 B1 | 4/2001 | Hsu et al. ................... 600/515 |
| 6,223,078 B1 | 4/2001 | Marcovecchio |
| 6,233,072 B1 | 5/2001 | Liu et al. ..................... 359/110 |
| 6,233,078 B1 | 5/2001 | Harano et al. ............. 359/134 |
| 6,233,487 B1 | 5/2001 | Mika et al. .................... 607/27 |
| 6,263,242 B1 | 7/2001 | Mika et al. .................... 607/9 |
| 6,266,554 B1 | 7/2001 | Hsu et al. ................... 600/515 |
| 6,275,732 B1 | 8/2001 | Hsu et al. ................... 607/14 |
| 6,301,503 B1 | 10/2001 | Hsu et al. ................... 607/30 |
| 6,308,095 B1 | 10/2001 | Hsu et al. |
| 6,312,388 B1 | 11/2001 | Marcovecchio et al. |
| 6,370,430 B1 | 4/2002 | Mika et al. .................... 607/9 |
| 6,430,435 B1 | 8/2002 | Hsu et al. ................... 600/518 |
| 6,434,417 B1 | 8/2002 | Lovett ........................ 600/509 |
| 6,449,503 B1 | 9/2002 | Hsu |
| 6,484,055 B1 | 11/2002 | Marcovecchio ................ 607/5 |
| 6,516,225 B1 | 2/2003 | Florio |
| 6,539,257 B1 * | 3/2003 | KenKnight ..................... 607/5 |
| 6,684,100 B1 | 1/2004 | Sweeney et al. |
| 2004/0010200 A1 | 1/2004 | Sweeny et al. |
| 2004/0093035 A1 | 5/2004 | Schwartz et al. |
| 2004/0127806 A1 | 7/2004 | Sweeney |
| 2004/0267143 A1 | 12/2004 | Sweeny |

OTHER PUBLICATIONS

Kinoshita, Shinji, et al., "Transient Disapperance of Complete Right Bundle Branch (BBB) During Exercise", *Journal of Electrocardiology*, vol. 29, No. 3, 1996, (1996), 255–256.

Ng, S. S., "Microcomputer–Based Telemetry System for ECG Monitoring", *IEEE Proc. of the Ann. Int'l Conf. of the Engineering in Medicine and Biology Society*, vol. Conf. 9, XP000015425, (1987), 1492–193.

Sweeney, Robert J., et al., "Tachyarrhythmia Detection and Discrimination Based on Curvature Parameters", U.S. Appl. No. 10/607,818, filed Jun. 27, 2003, 59 pgs.

* cited by examiner

USE OF CURVATURE BASED FEATURES FOR BEAT DETECTION

CROSS-REFERENCE TO RELATED APPLICATIONS

This application is related to co-pending, commonly assigned Sweeney et al. U.S. patent application Ser. No. 09/703,269, entitled "CURVATURE BASED METHOD FOR SELECTING FEATURES FROM AN ELECTRO-PHYSIOLOGICAL SIGNALS FOR PURPOSE OF COMPLEX IDENTIFICATION AND CLASSIFICATION," filed on Oct. 31, 2000, the specification of which is hereby incorporated by reference.

TECHNICAL FIELD

This document relates generally to cardiac rhythm management devices and particularly, but not by way of limitation, to such a device including a sensing system allowing beat detection.

BACKGROUND

Beat detection generally refers to detection of cardiac depolarizations. Detection of cardiac depolarizations is an important, often essential, part of cardiac signal analysis for diagnosing irregular or abnormal rhythms of a patient's heart. A heart functions as an electromechanical pump which forces blood to circulate throughout the body via the body's circulatory system to provide for the body's metabolic needs. The mechanical pumping function is accomplished with contractions of myocardium (heart muscles), which includes excitable tissues constructed of cardiac myocytes (contractile heart muscle cells). When the heart is at rest, the myocardium maintains a resting electrical potential through its cell membranes. In the absence of electrical current within the myocardium, two electrodes placed in or about the myocardium in its resting state would record no electrical signal. As the myocardium is excited by a sequence of electric events, self-propagating action potentials result from a complex cascade of electric currents that flow across the cell membranes. Consequently, a depolarizing wave of action potential sweeping through the myocardium is recorded by the two electrodes while causing the myocardium to contract. Thus, a cardiac depolarization is recorded by a pair of electrodes as an indication of a heart contraction, referred to as a heart beat. A beat can be detected by detecting the depolarization wave.

A temporal pattern of heart beats is known as cardiac rhythm. Depending on the location of the recording electrodes, cardiac rhythm reflects depolarizations at specific cardiac regions such as the right atrium, the left atrium, the right ventricle, and the left ventricle. In a normal heart, the depolarizations and other related cardiac events as recorded at various cardiac regions are well coordinated and synchronized with certain delays. When the heart functions irregularly or abnormally, however, the depolarizations and other related cardiac events as recorded at various cardiac regions may be chaotic and unsynchronized, indicating irregular or other abnormal cardiac rhythms, known as cardiac arrhythmias. Cardiac arrhythmias result in a reduced pumping efficiency of the heart, and hence, diminished blood circulation. Examples of such arrhythmias include bradyarrhythmias, that is, hearts that beat too slowly or irregularly, and tachyarrhythmias, that is, hearts that beat too quickly.

A cardiac rhythm management system includes a cardiac rhythm management device used to treat cardiac arrhythmia by delivering electrical pulses to the patient's heart. Cardiac rhythm management devices include, among other things, pacemakers, also referred to as pacers. Pacemakers are often used to treat patients with bradyarrhythmias. Such pacemakers may coordinate atrial and ventricular contractions to improve the heart's pumping efficiency. Cardiac rhythm management devices also include devices providing cardiac resynchronization therapy (CRT), such as for patients with congestive heart failure (CHF). CHF patients have deteriorated heart muscles that display less contractility and cause poorly synchronized heart contraction patterns. By pacing multiple heart chambers or multiple sites within a single heart chamber, the CRT device restores a more synchronized contraction of the weakened heart muscle, thus increasing the heart's efficiency as a pump. Cardiac management devices also include defibrillators that are capable of delivering higher energy electrical stimuli to the heart. Such defibrillators may also include cardioverters, which synchronize the delivery of such stimuli to portions of sensed intrinsic heart activity signals. Defibrillators are often used to treat patients with tachyarrhythmias. In addition to pacemakers, CRT devices, and defibrillators, cardiac rhythm management systems also include, among other things, pacer/defibrillators that combine the functions of pacemakers and defibrillators, drug delivery devices, and any other systems or devices for diagnosing or treating cardiac arrhythmias.

All modern cardiac rhythm management systems require detection of cardiac depolarizations to detect cardiac arrhythmias and to determine the nature of a detected cardiac arrhythmia and an appropriate therapy treating it. In one example, a fast, irregular pattern of ventricular depolarizations, known as R-waves, may indicate a ventricular fibrillation treatable by delivering a defibrillation pulse from a defibrillator. In another example, a heart having a normal atrial rhythm but poor atrioventricular synchrony can be resynchronized by pacing a ventricle following a predetermined delay after each atrial depolarization, known as a P-wave, is detected.

Therefore, a reliable beat detection, or detection of cardiac depolarizations, is essential to an accurate diagnosis of a cardiac arrhythmia and a successful and efficient administration of a therapy using a cardiac rhythm management system. Beat detection has been traditionally accomplished by using threshold criteria based on a first or second derivative of a sensed cardiac signal. A depolarization is detected whenever the amplitude of the cardiac signal exceeds such a threshold. Failure of detection occurs when, for example, noise is present, cardiac repolarizations (T-waves) are recorded as events having high amplitude or large slopes in the cardiac signal, and the slew-rate of the cardiac signal decreases.

For these and other reasons, the present inventors have recognized a need for ensuring a more reliable beat detection.

SUMMARY

A cardiac rhythm management system includes a sensing circuit to sense a cardiac signal and a sensing processor to detect cardiac depolarizations (beats) by utilizing certain morphological context of the sensed cardiac signal. In one embodiment, the morphological context of the sensed cardiac signal utilized in beat detection includes curvatures computed from the cardiac signal.

In one embodiment, the cardiac rhythm management system includes a sensing circuit to sense a cardiac signal, a sampling circuit to sample the cardiac signal on a continuous basis, a feature analyzer to derive cardiac signal features based on predetermined detection criteria, a counter to count the cardiac signal features over a predetermined period of time, and a comparator to detect a depolarization when the number of the cardiac signal features counted over the predetermined period of time exceeds the threshold number. The feature analyzer includes a curvature generator to compute cardiac curvatures of the cardiac signal on a sample-by-sample basis and a feature detector adapted to detect the cardiac signal features from the cardiac curvatures.

In another embodiment, the cardiac rhythm management system includes a sensing circuit to sense a cardiac signal, a sampling circuit to sample the cardiac signal on a continuous basis, a feature analyzer to derive cardiac signal features based on predetermined detection, a metric generator to compute a metric based on one or more of the cardiac signal features, and a metric comparator to provide an output signal indicating whether a depolarization has been detected based on the comparison between the metric and predetermined threshold criteria. The feature analyzer includes a curvature generator to compute curvatures of the cardiac signal on a sample-by-sample basis and a feature detector adapted to detect the cardiac signal features from the cardiac curvatures.

The approach to beat detection in both embodiments described above is referred to as feature-based beat detection. In one embodiment, the cardiac rhythm management system performs the feature-based beat detection in substantially real-time. In general, the feature-based beat detection can be used in all forms of cardiac signal sensing, including beat detection from an intracardiac electrogram and a surface ECG. The approach may also be used to detect various events from other time varying sensor signals, such as mechanical motion, sound, pressure, acceleration, or impedance signals.

BRIEF DESCRIPTION OF THE DRAWINGS

The drawings, which are not necessarily drawn to scale, illustrate generally, by way of example, but not by way of limitation, various embodiments discussed in the present document.

DETAILED DESCRIPTION

In the following detailed description, reference is made to the accompanying drawings that form a part hereof, and in which is shown, by way of illustration, specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

This document discusses, among other things, beat detection methods and apparatuses in applications involving cardiac rhythm management systems sensing a cardiac signal, including intracardiac electrogram or surface electrocardiogram (ECG). Such cardiac rhythm management systems include, but are not limited to, pacemakers, CRT devices, cardioverter/defibrillators, pacer/defibrillators, and drug delivery devices. However, it is to be understood that the present methods and apparatuses of heart beat detection may be employed in medical devices sensing other signals related to cardiac activities, including, but not being limited to, mechanical motion, sound, pressure, acceleration, or impedance signals.

Figure 1:
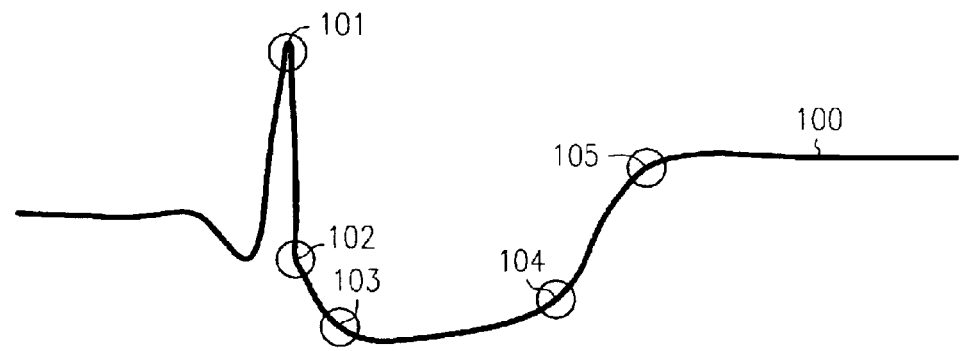
FIG. 1 is an illustration of a cardiac signal.

FIG. 1 is an illustration of a cardiac signal 100. In one embodiment, by way of example, but not by way of limitation, cardiac signal 100 is a portion of an intracardiac electrogram including a ventricular depolarization at point 101, known as an "R-wave." In one embodiment, by way of example, but not by way of limitation, beat detection includes R-wave detection. Traditionally, device-based beat detection from cardiac signal 100 is accomplished by using threshold criteria based on first or higher order derivatives of cardiac signal 100. One problem associated with such a traditional approach is that noise in cardiac signal 100 may be incorrectly detected as R-waves because the noise may have strong derivative values even if the amplitude of the noise is small as compared to the amplitude of cardiac signal 100. Another problem associated with the traditional approach is that T-waves, indicative of ventricular repolarizations, may be incorrectly detected as R-waves when the T-waves have relatively strong derivatives. These two problems are examples of what is generally known as oversensing. Yet another problem associated with the traditional approach is that true R-waves may not be detected when derivatives related to cardiac signal 100 decrease in value after the threshold criteria have been set. This may happen, for example, when the amplitude of the cardiac signal becomes small or when the slew rate of cardiac signal 100 decreases. This problem is an example of what is generally known as undersensing.

To address the problems of oversensing and undersensing, the present inventors have recognized that cardiac signal 100 contains contextual information allowing beat detection in addition to changes in the amplitude of cardiac signal 100, presence of certain noises, and/or changes in derivatives related to cardiac signal 100. In one embodiment, such contextual information is related to the morphology of cardiac signal 100. In one embodiment as shown in FIG. 1, one morphological characteristic of cardiac signal 100 is that the signal makes significant "turns." Examples of such significant turns include points 101–105. These points are different from the points that would be detected using a derivative-based criteria. For example, points 102–105 may not have amplitudes and/or derivatives that are significant enough to allow detection based on a derivative-based threshold criteria. However, points 101–105 all provide valuable morphological information, such as the times when cardiac signal 100 makes turns and the intensity (direction and sharpness) of each turn. In one embodiment, such morphological information allows beat detection by a device using a method based on the morphological context of cardiac signal 100. In one embodiment, points 101–105, representative of significant turns in cardiac signal 100, are each detected. Parameters such as time and intensity of each point can be measured to characterize the corresponding turn. In one embodiment, beat detection criteria are established based on such parameters related to one or more points, each representative of a significant turn in cardiac signal 100.

Figure 2:
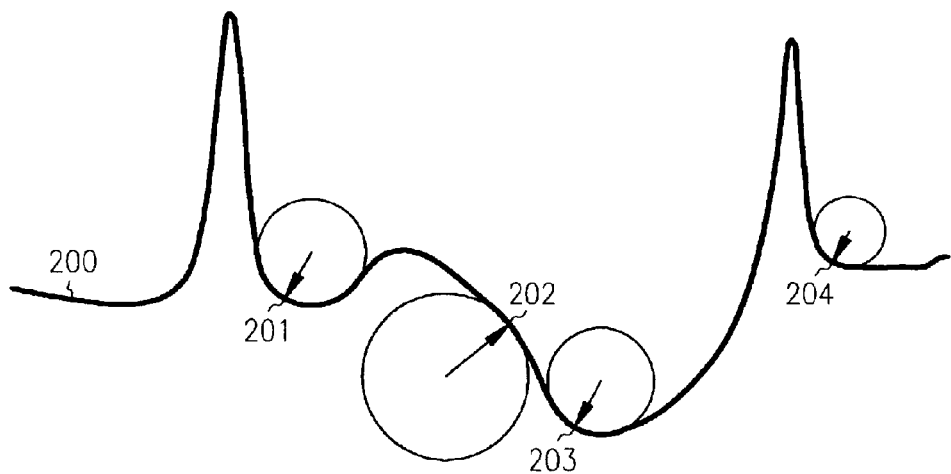
FIG. 2 is an illustration of a concept of cardiac signal curvature.

FIG. 2 is an illustration of a concept of cardiac signal curvature with another cardiac signal 200. In one embodiment, by way of example, but not by way of limitation, cardiac signal 200 is a portion of an intracardiac eletrogram. At any point along cardiac signal 200, a circle can be found that just fits the local portion of cardiac signal 200. The curvature at that point is inversely proportional to the radius of that circle. As illustrated in FIG. 2, with points 201–204 each associated with a fitting circle with a radius, sharper turns are associated with smaller circles, and hence larger curvature values, while milder turns are associated with larger circles, and hence smaller curvature values. In other words, curvature is a measure of the sharpness of a turn in cardiac signal 200. For example, cardiac signal 200 does not turn much at point 202, so the circle associated with point 202 is large and the curvature at point 202 is small. In contrast, cardiac signal 200 makes a sharp turn at point 204, so the circle associated with point 204 is small and the curvature at point 204 is large.

Assuming an arbitrary curve includes a point (X, Y) in a two-dimensional x-y space, the curvature of the arbitrary curve at point (X, Y) is defined as:

$$\text{Curvature} = (d^2Y/dX^2)/[1+(dY/dX)^2]^{3/2}.$$

In one embodiment, cardiac signal 200 is sampled in substantially real-time, and a curvature is computed on a sample-by-sample basis in substantially real-time to result in a cardiac curvature signal corresponding to cardiac signal 200 on the sample-by-sample basis. One embodiment of such real-time sample-by-sample curvature computation is disclosed in Sweeney et al., U.S. patent application Ser. No. 09/703,269, entitled "CURVATURE BASED METHOD FOR SELECTING FEATURES FROM AN ELECTRO-PHYSIOLOGICAL SIGNALS FOR PURPOSE OF COMPLEX IDENTIFICATION AND CLASSIFICATION," assigned to Cardiac Pacemakers, Inc., the disclosure of which is incorporated herein by reference in its entirety.

Figure 3:
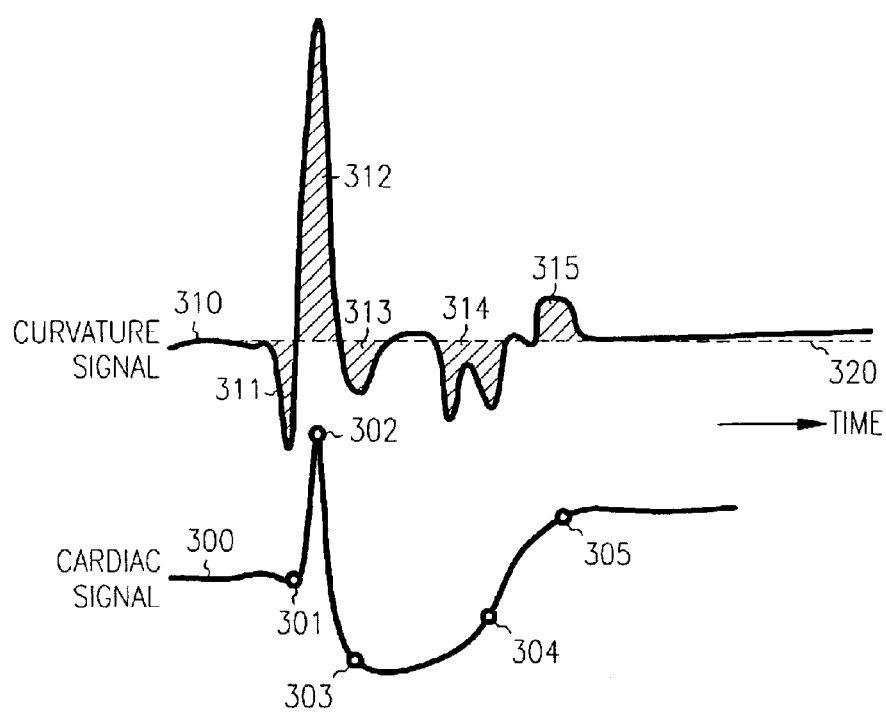
FIG. 3 is an illustration of curvature-based cardiac signal features.

FIG. 3 is an illustration of curvature-based cardiac signal features. A cardiac curvature signal 310 is computed on a sample-by-sample basis from a cardiac signal 300. To detect beats based on cardiac curvature signal 310, a stream of cardiac signal features, also referred to as significant points, are detected from cardiac curvature signal 310. A cardiac signal feature is a point associated with significant morphological information about cardiac signal 300 that allows beat detection based on morphological context of cardiac signal 300. In one embodiment, as discussed above, the cardiac signal features each represent a significant turn in cardiac signal 300. In one embodiment, a significant turn is a "fast" turn. Cardiac curvature signal 310 is compared to a predetermined threshold to detect the significant (fast) turns in cardiac signal 300. The predetermined threshold represents a minimum curvature for a turn to be considered significant. A cardiac signal feature representative of a significant turn is detected when a portion of cardiac curvature signal 310 exceeds the predetermined threshold.

In an alternative embodiment, as illustrated in FIG. 3, curvature signal 310 includes lobes 311–m315 each representing a single turn in cardiac signal 300. Lobes 311–315 are each formed between curvature signal 310 and a baseline 320. The area within each lobe reflects the total angle included in the corresponding turn and is referred to as the size of the turn. The location of each lobe with respect to baseline 320 is indicated as the direction of the turn. In one embodiment, a lobe has a positive direction if it is above baseline 320 or a negative direction if it is below baseline 320. The size and direction of each turn describes the intensity of the turn. In one embodiment, the centroid of the area within each lobe is computed. The time of the centroid is considered as the time of the turn. In one embodiment, each centroid is a cardiac signal feature. As illustrated in FIG. 3, cardiac signal features 301–305 are points occurring at times associated with the centroids of lobe 311–315, respectively. In one embodiment, amplitude of cardiac signal 300 at each of features 301–305 is measured. In one embodiment, the size of each lobe is compared to a threshold size. The lobes having sizes larger than the threshold size represent significant turns. In this embodiment, the significant turns are "big" turns. Cardiac signal feature parameters, including the size, direction, and centroid, are computed only for such significant (big) turns, which are represented by the cardiac signal features.

To summarize, a cardiac signal feature is a morphologically significant point representative of a turn in cardiac signal 300, at which at least feature-related parameters including the time of the occurrence of the cardiac signal feature, cardiac signal amplitude at the time of the occurrence of the cardiac signal feature, and the intensity of the turn can be measured and/or calculated. The intensity of the turn is described by the direction and the size of the turn. In one embodiment, beats are detected based on one or more cardiac signal features each associated with one or more feature-related parameters.

Figure 4:
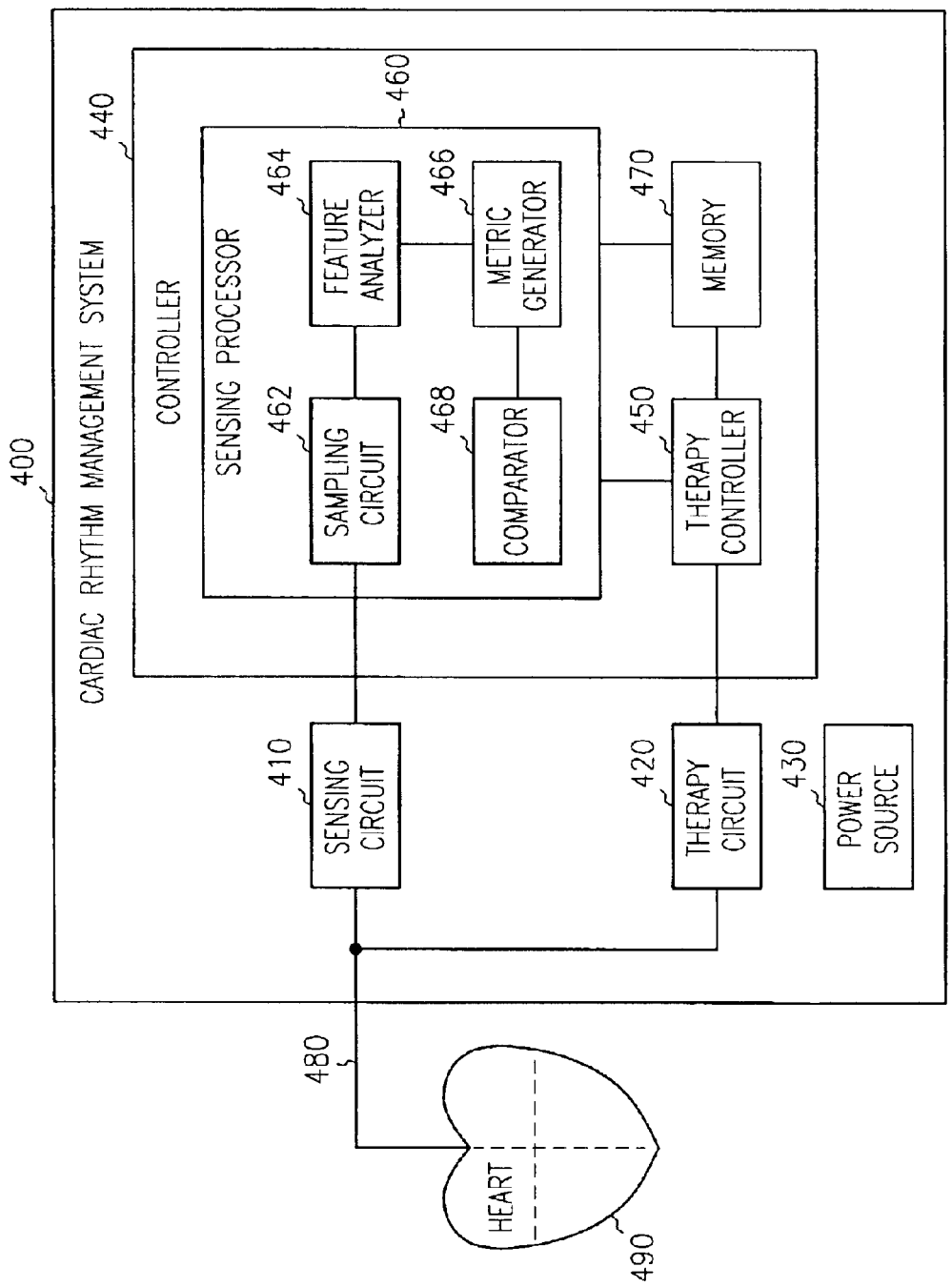
FIG. 4 is a schematic/block diagram illustrating one embodiment of portions of a cardiac rhythm management system that performs heart beat detection using the curvature-based cardiac signal features.

FIG. 4 is a schematic/block diagram illustrating one embodiment of portions of a cardiac rhythm management system that performs beat detection using curvature-based cardiac signal features. In this embodiment, a cardiac rhythm management system 400 senses cardiac activities from a heart 490 and delivers one or more therapies to heart 490 when a need for such therapy or therapies is indicated by the sensed cardiac activities. A lead 480 provides for an electrical connection between cardiac rhythm management system 400 and heart 490. In one embodiment, lead 480 is an intracardiac lead having at least one electrode adapted to be disposed in or about heart 490. Cardiac rhythm management system 400 includes, but is not limited to, one or more of pacemakers, CRT devices, cardioverter/defibrillators, pacer/defibrillators, and drug delivery devices. In one embodiment, cardiac rhythm management system 400 includes a sensing circuit 410 to sense the cardiac activities from heart 490, a therapy circuit 420 to deliver the one or more therapies to heart 490, a power source 430 to energize all components of cardiac rhythm management system 400, and a controller 440. Controller 440 includes a therapy controller 450 to control the delivery of the one or more therapies, a sensing processor 460 to process the sensed cardiac activities, and a memory 470 to store at least instructions for the operation of cardiac rhythm management system 400 and data related to the sensed cardiac activities. In one embodiment, therapy controller 450 determines whether to deliver a therapy and/or the time for delivering the therapy based on beat detection performed by sensing processor 460.

In one embodiment, sensing processor 460 includes a sampling circuit 462, a feature analyzer 464, a metric generator 466, and a comparator 468. In one embodiment, sensing processor 460 provides for detection of cardiac events from heart 490. In one embodiment, sensing processor 460 provides for detection of cardiac depolarizations from heart 490. In one embodiment, sampling circuit 462 samples a cardiac signal at a predetermined sampling rate to produce a sampled cardiac signal. In a further embodiment, sampling circuit 462 further calculates a moving average based on a predetermined number of the most recent samples to produce a moving-averaged sampled cardiac signal. In one embodiment, each moving-averaged sample is computed based on three most recently taken samples. In one embodiment, feature analyzer 464 comprises a curvature generator and a feature detector. The curvature generator computes a curvature based on a predetermined number of most recently-taken samples from the sampled cardiac signal after each sample is taken by sampling circuit 462. In an alternative embodiment, the curvature generator computes a curvature based on a predetermined number of the most recent moving-averaged samples from the moving-averaged sampled cardiac signal after each moving-averaged sample is computed by sampling circuit 462. In both embodiments, a cardiac curvature signal corresponding to the cardiac signal is produced. Then, the feature detector detects cardiac signal features from the cardiac curvature signal based on predetermined criteria. In one embodiment, the feature detector detects cardiac signal features when the amplitude of the cardiac curvature signal exceeds a predetermined threshold. Such cardiac signal features represent fast turns in the cardiac signal. In a further embodiment, a beat is detected when the feature detector detects a fast turn of the cardiac signal, such as an R-wave, with the predetermined threshold set high enough to detect only the fastest turn during each cardiac cycle. In another embodiment, the feature detector computes cardiac signal features that are each a point temporally corresponding to a centroid of a lobe of the cardiac curvature signal, where the lobe is formed between the cardiac curvature signal and its baseline, as described above with respect to FIG. 3. In this embodiment, the feature detector includes a zero-crossing detector, a direction detector, a size calculator, and a centroid locator. The zero-crossing detector identifies the lobes by detecting the beginning and the end of each lobe in the cardiac curvature signal, which correspond to the points of time when the cardiac curvature signal crosses its baseline. In one embodiment, the baseline represents a voltage level equal to or near 0 V. In one embodiment, the zero-crossing detector operates with a hysteresis such that a lobe only begins when the curvature signal reaches a threshold slightly away from the baseline and ends when it crosses the baseline or reaches another threshold near the baseline. This eliminates excessive computations by feature analyzer 464 caused by many small, insignificant turns in the cardiac signal. After the lobes are identified, the direction detector determines whether each lobe is above or below the baseline and respectively records the outcome as a positive or negative direction. Then, the size calculator computes an approximate area within each lobe. This approximate area is referred to as the size of the cardiac signal feature. The centroid locator temporally locates the centroid of the area within the lobe. An approximate time of the centroid is then taken as the time when a cardiac signal feature occurs in the cardiac signal. In one embodiment, feature analyzer 464 measures the amplitude of the cardiac signal when each cardiac signal feature occurs in the cardiac signal. In one embodiment, feature analyzer 464 outputs feature-related parameters including the time when each cardiac signal feature occurs, the amplitude of the cardiac signal when the cardiac signal feature occurs, the direction of the feature, and the size of the cardiac signal feature. The direction and size describe the intensity of a cardiac signal feature, i.e., the intensity of a turn in the cardiac signal. Metric generator 466 generates a metric based on one or more of the cardiac signal features. The metric is a measure indicative of whether a predetermined cardiac event has occurred. In one embodiment, the metric allows beat detection by comparing the metric to a predetermined threshold. In one embodiment, metric generator 466 includes a counter to count the number of cardiac signal features derived from the cardiac curvature signal within a predetermined period of time. In this embodiment, the metric represents the number of cardiac signal features, indicative of the number of turns in the cardiac signal occurring, within the predetermined period of time. In a further embodiment, metric generator 466 includes a counter that counts a cardiac signal feature when the cardiac signal feature size exceeds a predetermined level. In this embodiment, the metric is indicative of the number of intense turns in the cardiac signal occurring within the predetermined period of time. In another embodiment, metric generator 466 includes an arithmetic module to compute the metric based on one or more of the feature-related parameters output by feature analyzer 464. The metric is a value that allows beat detection by comparing the value to a predetermined threshold. In one embodiment, the arithmetic module computes the metric by using an empirically derived equation. One example of such an equation is:

$$\text{Metric}=|A(n)D(n)-A(n-1)D(n-1)||Y(n)-Y(n-1)|/[X(n)-X(n-1)],$$

where n denotes a "current" cardiac signal feature and n−1 denotes the cardiac signal feature immediately preceding the "current" feature, X is the time of occurrence of the cardiac signal feature, A is the size of the cardiac signal feature, D is the direction of the cardiac signal feature (having a value of either 1 or −1, respectively indicative of positive or negative direction), and Y is the amplitude in the cardiac signal at the time of the feature. The metric computed using this equation amplifies the morphological changes in the cardiac signal as indicated by the parameters related to two adjacent cardiac signal features.

Comparator 468 allows feature-based detection of cardiac events. In one example, comparator 468 includes a signal input representative of the metric output from metric generator 466, a reference input representative of a predetermined threshold, and an output indicative of whether a beat is detected. In one embodiment, the predetermined threshold is empirically derived. In one embodiment, the predetermined threshold is a fixed value programmed into cardiac rhythm management system 400 and remains constant until being re-programmed. In another embodiment, the predetermined threshold is being automatically adjusted in response to changes in the cardiac signal. In the embodiment in which the metric represents the number of cardiac signal features within a predetermined period of time, comparator 468 compares the metric to a threshold representing a predetermined number of cardiac signal features within the predetermined period of time. A beat is detected whenever the number of cardiac signal features within the predetermined period of time exceeds the threshold. In the embodiment in which the metric is computed from the feature-related parameters using an arithmetic module, comparator 468 compares the metric to a threshold above which the metric is indicative of an occurrence of a beat.

In one embodiment, sensing processor 460 is a substantially real-time processor of the sensed cardiac activities. The components of sensing processor 460, including sampling circuit 462, feature analyzer 464, metric generator 466, comparator 468, and their sub-components, operate in substantially real-time to provide for a substantially real-time beat detection using curvature-based cardiac signal features.

Figure 5:
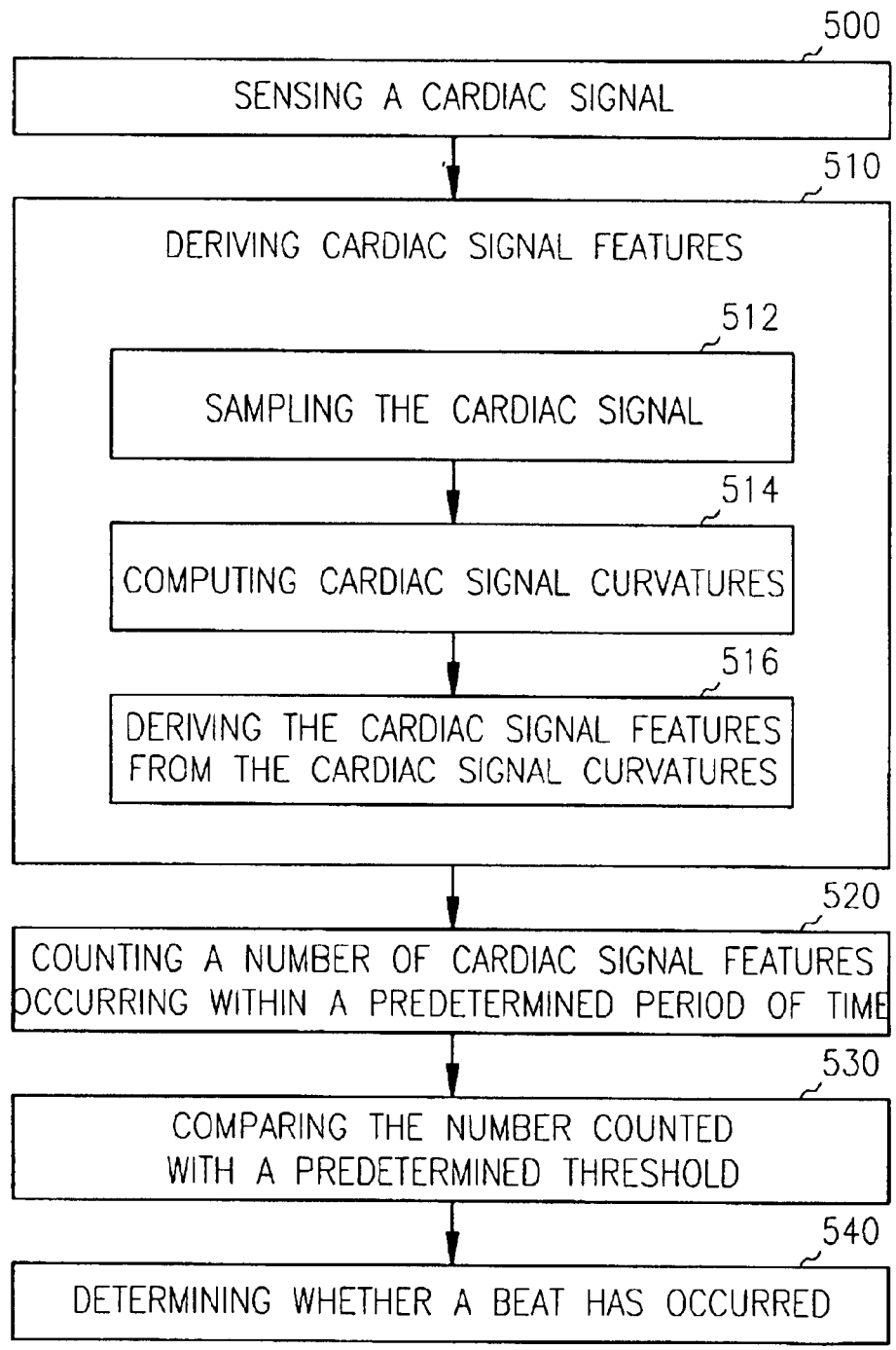
FIG. 5 is a flow chart illustrating one embodiment of a method of beat detection corresponding to the embodiment of FIG. 4.

FIG. 5 is a flow chart illustrating one embodiment of a method of beat detection corresponding to the embodiment of FIG. 4. At 500, sensing circuit 410 senses a cardiac signal. At 510, cardiac signal features are derived from the cardiac signal. In one embodiment, the cardiac signal features are derived from cardiac signal curvatures computed from the cardiac signal. In this embodiment, sampling circuit 462 samples the sensed cardiac signal at a predetermined sampling rate at 512. Feature analyzer 464 computes cardiac signal curvatures on a continuous sample-by-sample basis from the sampled cardiac signal at 514. This results in a cardiac curvature signal corresponding to the cardiac signal. At 516, feature analyzer 464 derives the cardiac signal features from the cardiac curvature signal. In one embodiment, each cardiac signal feature is derived by comparing the cardiac signal curvature to a predetermined threshold and represents a significant turn in the cardiac signal. In another embodiment, each cardiac signal feature corresponds to a centroid of a lobe of the curvature signal, as described above with respect to FIG. 3. At 520, metric generator 466 counts the number of cardiac signal features occurring during a predetermined period of time. This predetermined period of time is sufficiently short to avoid any excessive delay in beat detection. In one embodiment, the predetermined period of time is a fraction of the time interval between two consecutive beats. In one embodiment, the predetermined period of time is about 50 ms. Comparator 468 compares the number of cardiac signal features counted to a predetermined threshold at 530, and determines that a beat has occurred when the number of cardiac signal features counted during the predetermined period of time exceeds the predetermined threshold at 540. In one embodiment, all the steps in FIG. 5 are performed in substantially real-time to provide for a substantially real-time beat detection using curvature-based cardiac signal features.

Figure 6:
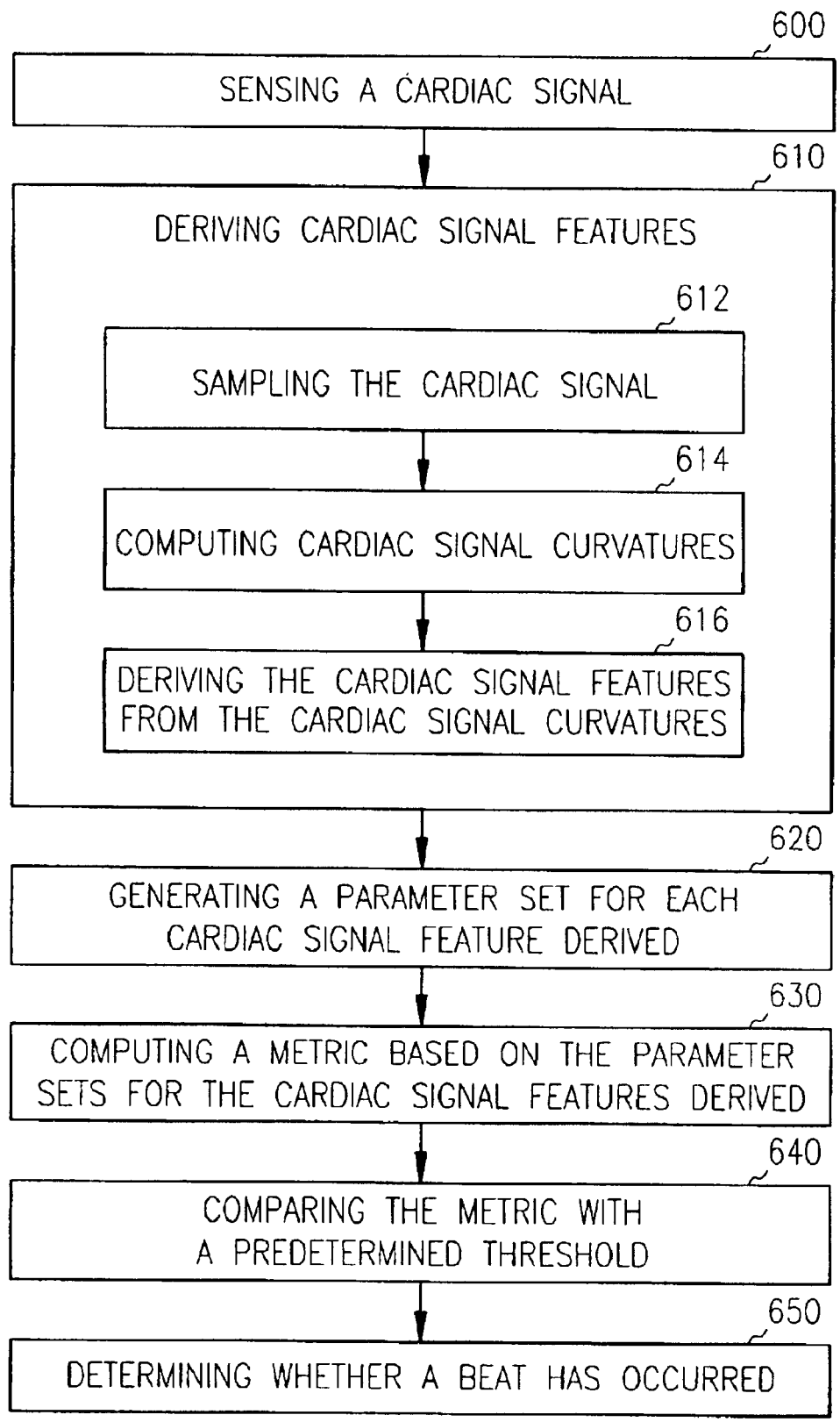
FIG. 6 is a flow chart illustrating another embodiment of a method of beat detection corresponding to the embodiment of FIG. 4.

FIG. 6 is a flow chart illustrating another embodiment of a method of beat detection corresponding to the embodiment of FIG. 4. At 600, sensing circuit 410 senses a cardiac signal. At 610, cardiac signal features are derived from the cardiac signal. In one embodiment, the cardiac signal features are derived from cardiac signal curvatures computed from the cardiac signal. In this embodiment, sampling circuit 462 samples the sensed cardiac signal at a predetermined sampling rate at 612. Feature analyzer 464 computes cardiac signal curvatures on a continuous sample-by-sample basis from the sampled cardiac signal at 614. This results in a cardiac curvature signal corresponding to the cardiac signal. At 616, feature analyzer 464 derives the cardiac signal features from the cardiac curvature signal. In one embodiment, each feature is derived by comparing the cardiac signal curvature to a predetermined threshold and represents a significant turn in the cardiac signal. In another embodiment, each cardiac signal feature corresponds to a centroid of a lobe of the cardiac curvature signal, as described above with respect to FIG. 3. At 620, feature analyzer 464 generates a parameter set associated with each cardiac signal feature. In one embodiment, the parameter set associated with each cardiac signal feature includes one or more of the time when the cardiac signal feature occurs, the amplitude of the cardiac signal at the time when the cardiac signal feature occurs, and the intensity of the cardiac signal feature. The intensity of the cardiac signal feature includes the direction and the size of the cardiac signal feature. Metric generator 466 computes a metric based on one or more parameters included in the parameter sets associated with cardiac signal features at 630. Comparator 468 compares the metric with a predetermined threshold at 640 and determines whether a depolarization has occurred at 650 based on the comparison. In one embodiment, this predetermined threshold is empirically determined. In one embodiment, the predetermined threshold is a fixed value programmed into cardiac rhythm management system 400. The value remains fixed until being re-programmed. In an alternative embodiment, the predetermined threshold is self-adjusting after being programmed to adapt to changes in the cardiac signal after the programming. In one embodiment, all the steps in FIG. 6 are performed in substantially real-time to provide for a substantially real-time beat detection using curvature-based cardiac signal features.

Beat detection using morphologically significant features in a cardiac signal, also referred to as feature-based beat detection, uses more complete signal information than the traditional beat detection using time derivative-based threshold criteria. The process of deriving the features filters noise from the cardiac signal without altering the overall morphological characteristic of the cardiac signal. The feature-based beat detection is not directly dependent on the amplitude or slope of the cardiac signal. Thus, a single instance of high derivatives, such as with a noise spike, does not trigger a feature-based beat detection even though it may trigger a beat detection in a traditional approach using threshold criteria dependent on the first and higher derivatives of the cardiac signal.

Feature-based beat detection can be used in all forms of cardiac signal sensing, including beat detection from an intracardiac electrogram and a surface ECG. The approach may also be used to detect various events from other time varying sensor signals, such as mechanical motion, sound, pressure, acceleration, or impedance signals. In addition to beat detection, feature-based beat detection may also be used to detect other beat-related events, such as heart contraction and cardiac valve functions. In one embodiment, feature-based beat detection is the primary beat detection method used in a cardiac rhythm management system. In another embodiment, feature-based beat detection is used to verify the reliability of a beat detection using a different detection method, such as the traditional approach described above with respect to FIG. 1. In yet another embodiment, feature-based beat detection is used for short periods of beat detection in supplement to a primary detection method, such as the traditional approach described above with respect to FIG. 1.

It is to be understood that the above detailed description is intended to be illustrative, and not restrictive. For example, beat detection can be included in the operation of any medical device in which heart rate is monitored. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A system, comprising:
   a sensing circuit to sense a cardiac signal;
   a sampling circuit, coupled to the sensing circuit, to sample the cardiac signal on a continuous basis;

a feature analyzer, coupled to the sampling circuit, to generate a cardiac curvature signal based on the cardiac signal and detect cardiac signal features from the cardiac curvature signal based on predetermined detection criteria;

a counter, coupled to the feature analyzer, to count the cardiac signal features over a predetermined period of time; and a comparator, coupled to the counter, to receive a first input representative of a number of the cardiac signal features counted over the predetermined period of time and compare that input to a second input representative of a predetermined threshold number, and to provide a depolarization indicating signal when the number of the cardiac signal features counted over the predetermined period of time exceeds the threshold number.

2. The system of claim 1, further comprising a therapy circuit, coupled to the comparator, to trigger or inhibit a delivery of a cardiac therapy based on the depolarization indicating signal.

3. The system of claim 1, wherein the feature analyzer comprises:

a curvature generator, coupled to the sampling circuit, to generate a cardiac curvature signal corresponding to the cardiac signal by computing a curvature, after each sample is taken, based on the each sample and a predetermined number of preceding samples; and a feature detector adapted to detect the cardiac signal features from the cardiac curvature signal.

4. The system of claim 3, further comprising an intracardiac electrode coupled to the sensing circuit.

5. The system of claim 3, wherein the feature detector comprises a feature comparator adapted to compare an amplitude of the cardiac curvature signal to a predetermined threshold amplitude and generate a signal indicating that a cardiac signal feature has been detected when the amplitude of the cardiac curvature signal exceeds the predetermined threshold amplitude.

6. The system of claim 3, wherein the feature detector comprises:

a zero-crossing detector to detect lobes of the cardiac curvature signal, the lobes each including a beginning time when the cardiac curvature signal reaches a first threshold and an ending time when the cardiac curvature signal reaches a second threshold, the first and second thresholds each being slightly away from or approximately equal to a baseline of the cardiac curvature signal;

a size calculator to calculate an approximate area between the cardiac curvature signal and the baseline for each of the lobes, and a centroid locator to temporally locate a centroid of the calculated approximate area of the each of the lobes, the centroid indicative of an approximate time of occurrence of one of the cardiac signal features representing the each of the lobes.

7. A system comprising:

a sensing circuit to sense a cardiac signal;

a sampling circuit, coupled to the sensing circuit, to sample the cardiac signal on a continuous basis;

a feature analyzer, coupled to the sampling circuit, to generate a cardiac curvature signal based on the cardiac signal and detect cardiac signal features from the cardiac curvature signal based on predetermined detection criteria;

a metric generator, coupled the feature analyzer, to compute a metric based on one or more of the cardiac signal features; and a metric comparator, coupled to the metric generator, to receive a first metric input representative of the metric and compare that input to a second metric input representative of a predetermined threshold, and to provide an output signal indicating whether a depolarization has been detected.

8. The system of claim 7, further comprising a therapy circuit, coupled to the metric comparator, to trigger or inhibit a delivery of a cardiac therapy based on the output signal indicating whether the depolarization has been detected.

9. The system of claim 7, wherein the feature analyzer comprises:

a curvature generator, coupled to the sampling circuit, to generate a cardiac curvature signal corresponding to the cardiac signal by computing a curvature, after each sample is taken, based on the each sample and a predetermined number of preceding samples; and a feature detector adapted to detect the cardiac signal features from the cardiac curvature signal.

10. The system of claim 9, further comprising an intracardiac electrode coupled to the sensing circuit.

11. The system of claim 9, wherein the feature detector comprises a feature comparator adapted to compare an amplitude of the cardiac curvature signal to a predetermined threshold amplitude and generate a signal indicating that one of the cardiac signal features has occurred when the amplitude of the cardiac curvature signal exceeds the predetermined threshold amplitude.

12. The system of claim 9, wherein the feature detector comprises:

a zero-crossing detector to detect lobes of the cardiac curvature signal, the lobes each identifying one of the cardiac signal features and including a beginning time when the cardiac curvature signal reaches a first threshold and an ending time when the cardiac curvature signal reaches a second threshold, the first and second threshold each being slightly away from or approximately equal to a baseline of the cardiac curvature signal;

a direction detector to determine a direction of each of the cardiac signal features, the direction indicative of whether one of the lobes identifying the each of the cardiac signal features is above or below the baseline;

a size calculator to calculate a size of the each of the cardiac signal features, the size being an approximate area between the cardiac curvature signal and the baseline for the one of the lobes; and a centroid locator to temporally locate a centroid of the calculated approximate area of the one of the lobes, the centroid indicative of an approximate time of occurrence of the each of the cardiac signal features representing the one of the lobes.

13. The system of claim 12, wherein the feature analyzer comprises an amplitude detector adapted to measure an amplitude of the cardiac signal at the approximate time of occurrence of the each of the cardiac signal features.

14. The system of claim 13, wherein the metric generator comprises an arithmetic module adapted to compute the metric based on one or more of the cardiac signal features.

15. The system of claim 14, wherein the arithmetic module is adapted to compute the metric based on at least one of the approximate time of occurrence, the size, the direction, and the amplitude of the cardiac signal associated with each of the one or more of the cardiac signal features.

16. A method comprising:
sensing a cardiac signal;
computing curvatures based on the cardiac signal;
deriving cardiac signal features from the computed curvatures;
counting a number of the cardiac signal features over a predetermined period of time; and
determining that a depolarization has occurred when the number of the cardiac signal features counted over the predetermined period of time exceeds a predetermined threshold number.

17. The method of claim 16, further comprising triggering or inhibiting a cardiac therapy when the depolarization has occurred.

18. The method of claim 16, wherein deriving the cardiac signal features comprises identifying portions of the cardiac signal having at least one predetermined morphological characteristic.

19. The method of claim 18, wherein the sensing, deriving, computing, counting, and determining comprise sensing, computing, deriving, counting, and determining in substantially real-time.

20. The method of claim 18, wherein computing the curvatures comprises:
sampling the cardiac signal; and
computing curvatures on a continuous, sample-by-sample basis, based on the sampled cardiac signal.

21. The method of claim 20, wherein computing the curvatures comprises computing a curvature after completion of taking of each sample of the cardiac signal, based on the each sample and a predetermined number of samples preceding the each sample.

22. The method of claim 21, wherein deriving the cardiac signal features comprises comparing the curvatures with a predetermined threshold.

23. The method of claim 21, wherein computing the curvatures further comprises generating a cardiac curvature signal corresponding to the cardiac signal, and wherein deriving the cardiac signal features comprises computing an approximate centroid of each lobe of the cardiac curvature signal, the each lobe including an area between the cardiac curvature signal and a baseline of the cardiac curvature signal between a first point of time when the cardiac curvature signal reaches a first threshold and a second point of time when the cardiac curvature signal reaches a second threshold, the first and second thresholds each being slightly away from or approximately equal to the baseline.

24. A method comprising:
sensing a cardiac signal;
deriving cardiac signal features;
generating a parameter set associated with each of the cardiac signal features;
computing a metric based on portions of the parameter sets associated with the cardiac signal features;
comparing the metric with a predetermined threshold; and
determining whether a depolarization has occurred based on an outcome of the comparing.

25. The method of claim 24, further comprising determining whether to deliver a cardiac therapy based on whether the depolarization has occurred.

26. The method of claim 24, wherein deriving the cardiac signal features comprises identifying portions of the cardiac signal having at least one predetermined morphological characteristic.

27. The method of claim 26, wherein the sensing, deriving, generating, computing, comparing, and determining comprise, respectively, sensing, deriving, generating, computing, comparing, and determining in substantially real-time.

28. The method of claim 26, wherein deriving the cardiac signal features comprises:
sampling the cardiac signal;
computing curvatures on a continuous basis, based on the sampled cardiac signal; and
deriving the cardiac signal features from the computed curvatures.

29. The method of claim 28, wherein computing curvatures comprises computing a curvature after completion of taking of each sample of the cardiac signal, based on the each sample and a predetermined number of samples preceding the each sample.

30. The method of claim 29, wherein deriving the cardiac signal features comprises comparing the curvatures with a predetermined threshold.

31. The method of claim 29, wherein computing curvatures further comprises generating a cardiac curvature signal corresponding to the cardiac signal, and wherein deriving the cardiac signal features comprises computing an approximate centroid of each lobe of the cardiac curvature signal, the each lobe including an area between the cardiac curvature signal and a baseline of the cardiac curvature signal between a first point of time when the cardiac curvature signal reaches a first threshold and a second point of time when the cardiac curvature signal reaches a second threshold, the first and second thresholds each being slightly away from or approximately equal to the baseline.

32. The method of claim 24, wherein computing the metric comprises using an arithmetic formula to compute the metric based on one or more of the cardiac signal features each associated with one or more parameters.

33. The method of claim 32, wherein determining whether the depolarization has occurred comprises:
comparing the metric with a predetermined threshold; and
producing a depolarization signal when the metric exceeds the predetermined threshold.

34. The method of claim 33, wherein deriving the cardiac signal features comprises:
sampling the cardiac signal;
computing curvatures on a continuous basis, based on the sampled cardiac signal, to generate a cardiac curvature signal corresponding to the cardiac signal; and
computing approximate centroids of lobes of the cardiac curvature signal, the lobes each identifying one of the cardiac signal features and including an area between the cardiac curvature signal and a baseline of the cardiac curvature signal between a first point of time when the cardiac curvature signal reaches a first threshold and a second point of time when the cardiac curvature signal reaches a second threshold, the first and second thresholds each being slightly away from or approximately equal to the baseline.

35. The method of claim 34, wherein computing the metric comprises using the arithmetic formula to compute the metric based on one or more of the cardiac signal features each representing one of the approximate centroids computed from one of the lobes and associated with at least one of:
an approximate time of occurrence;
an amplitude of the cardiac signal at the approximate time of the occurrence;
a direction representative of whether the one of the lobes is positive or negative with respect to the baseline; and a size representative of an approximate area of the one of the lobes.

36. A method, comprising:

receiving a sensor signal;

computing a curvature signal corresponding to the sensor signal;

deriving signal features based on the curvature signal; and determining whether a predetermined physiological event has occurred based on the signal features.

37. The method of claim 36, wherein receiving the sensor signal comprises receiving at least one of:

an intracardiac electrogram signal;

an electrocardiogram (EGG) signal;

a mechanical motion signal;

a sound signal;

a pressure signal;

an acceleration signal; and an impedance signal.

38. The method of claim 37, wherein determining whether the predetermined physiological event has occurred comprises determining whether a cardiac depolarization has occurred.

39. The method of claim 38, further comprising determining whether to deliver a cardiac therapy based on an outcome of the determining whether the cardiac depolarization has occurred.

* * * * *

UNITED STATES PATENT AND TRADEMARK OFFICE
CERTIFICATE OF CORRECTION

PATENT NO. : 6,950,702 B2 Page 1 of 1
APPLICATION NO. : 10/195838
DATED : September 27, 2005
INVENTOR(S) : Sweeney It is certified that error appears in the above-identified patent and that said Letters Patent is hereby corrected as shown below:

In column 13, line 19, in Claim 19, after "sensing," insert -- computing, --.

In column 13, line 20, in Claim 19, after "deriving," delete "computing,".

In column 15, line 14, in Claim 37, delete "(EGG)" and insert -- (ECG) --, therefor.

Signed and Sealed this

Twenty-third Day of January, 2007

JON W. DUDAS
*Director of the United States Patent and Trademark Office*